United States Patent
Kashiwagi et al.

(10) Patent No.: US 6,896,668 B2
(45) Date of Patent: May 24, 2005

(54) NAPKIN PACKAGE

(75) Inventors: Masahiro Kashiwagi, Kagawa (JP); Tatsuya Tamura, Kagawa (JP); Shinnpei Komatsu, Kagawa (JP)

(73) Assignee: Uni-Charm Corporation, Kawanoe (JP)

( * ) Notice: Subject to any disclaimer, the term of this patent is extended or adjusted under 35 U.S.C. 154(b) by 517 days.

(21) Appl. No.: 10/187,807

(22) Filed: Jul. 3, 2002

(65) Prior Publication Data
US 2003/0014032 A1 Jan. 16, 2003

(30) Foreign Application Priority Data
Jul. 13, 2001 (JP) .................................. 2001-213200

(51) Int. Cl.[7] .............................................. A61F 13/15
(52) U.S. Cl. ....................... 604/385.02; 604/385.02; 604/385.01; 604/385.201
(58) Field of Search ................. 604/385.02, 385.01, 604/385.03, 385.04, 385.201; 206/440, 581, 438, 823, 812, 494, 457

(56) References Cited

FOREIGN PATENT DOCUMENTS

| JP | 2001-037804 | 2/2001 | ......... | A61F/13/472 |
| WO | WO-01/24748 A1 | 4/2001 | | |

OTHER PUBLICATIONS

Patent Abstracts of Japan, Individually Packing Structure of Absorbent Article, Publication No. 2001–037804, Publication Date Feb. 2001.

Primary Examiner—Jacqueline Stephens
(74) Attorney, Agent, or Firm—Darby & Darby

(57) ABSTRACT

A napkin package is difficult to form permanent folding, twisting or corrugation in a leakage preventing wall as folded and wrapped by a packaging sheet, to ensure raising of the leakage preventing wall from a surface of a sanitary napkin after opening the package for achieving satisfactory side leakage preventing effect. A sanitary napkin has longitudinally extending leakage preventing walls on both sides of a liquid absorbing portion. A reinforcement sheet is provided on a surface side of a folded sanitary napkin with covering a portion of the folding line, the reinforcement sheet is bent at a position corresponding to the folding line without forming crease, and portions of the leakage preventing walls located corresponding to the portion across which the folding line extends, are urged onto an outer surface of the bent portion of the reinforcement sheet by the elastic tension force.

6 Claims, 7 Drawing Sheets

NAPKIN PACKAGE

BACKGROUND OF THE INVENTION

1. Field of the Invention

The present invention relates generally to a napkin package wrapping a sanitary napkin in a packaging sheet in folded condition. More particularly, the invention relates to a napkin package which can prevent twisting or deformation of leakage preventing wall provided on a surface of the sanitary napkin in wrapped condition.

2. Description of the Related Art

Each sanitary napkin is independently wrapped by a packaging sheet in order to keep in sanitary condition. In a napkin package, a longitudinally elongated sanitary napkin is folded at laterally extending two or three folding lines and wrapped by a packaging sheet formed from a resin film and the like.

On the other hand, some type sanitary napkins are formed with longitudinally extending leakage preventing walls on both side portions of a surface serving as liquid absorbing surface ("liquid absorbing surface" is also referred to as body facing surface). The leakage preventing wall is formed from a hydrophobic non-wovenfabric. To the leakage preventing wall, an elastic member for providing elastic tension force in the longitudinal direction is attached for causing bowing of the sanitary napkin. As a result, a free edge portion of the leakage preventing wall is raised away from the surface of the sanitary napkin.

In the sanitary napkin package, the sanitary napkin is folded at two or three folding lines in consideration of convenience of carrying (i.e., portability). Therefore, the folding line can be set across the leakage preventing wall, on which the elastic tension force is acting. When the leakage preventing wall applied elastic tension force is folded, the leakage preventing wall can be folded irregularly at the folding line to form permanent folding and to leave permanent twisting or corrugation in some folding conditions.

Maintaining the sanitary napkin in folded condition for a long period results in leaving of permanent folding, permanent twisting or corrugation. Then, when the sanitary napkin is taken out with opening the packaging sheet, it becomes uncertain if the leakage preventing wall is raised to possibly degrade side leakage blocking effect by the leakage preventing wall.

On the other hand, in Japanese Unexamined Patent Publication No. 2001-37804, there has been pointed out the problem in that when the sanitary napkin is folded at the portion where the elastic tension force of the leakage preventing wall is acting, elastic tension force of the elastic member provided on the leakage preventing wall can be weaken. In the invention disclosed in the above-identified publication, there has been proposed to provide the leakage preventing wall having regions where the elastic member is not provided so that the sanitary napkin is folded at the portion where the elastic member is not provided.

However, in the invention disclosed in the above identified publication, since the sanitary napkin is folded in the region of the leakage preventing wall where the elastic member is not provided, twisting or corrugation can be formed in the leakage preventing wall at the folded portion. Also, after opening the package, the leakage preventing wall at the folded portion cannot be raised by the elastic force. Therefore, the sanitary napkin is fitted on the wearer's body in a condition where the twisting or corrugation is left in the leakage preventing wall. On the other hand, when tight fitting force is applied on the sanitary napkin in the condition fitted on the wearer's body, the leakage preventing wall can be fallen down or crushed at the portions where the elastic member is absent. Then, since the elastic member is not provided, restoring force cannot be applied to the fallen down or crushed portion. For the reason set forth above, the leakage preventing wall cannot achieve satisfactory side leakage blocking effect.

SUMMARY OF THE INVENTION

The present invention has been worked out in view of the shortcoming in the prior art. Therefore, it is an object of the present invention to provide a napkin package which is difficult to form permanent folding, twisting or corrugation in a leakage preventing wall as folded and wrapped by a packaging sheet, to ensure raising of the leakage preventing wall from a surface of the sanitary napkin after opening the package for achieving satisfactory side leakage blocking effect.

According to the first aspect of the present invention, a napkin package is formed by wrapping a sanitary napkin in folded condition with a packaging sheet, wherein the sanitary napkin has longitudinally extending leakage preventing walls on both sides of a liquid absorbing portion, the leakage preventing walls are provided with elastic members for applying an elastic tension force in a longitudinal direction to place free edge portions of the leakage preventing walls away from a surface of the liquid absorbing portion;

the sanitary napkin is folded along a folding line extending across the leakage preventing walls with mating the surface;

a reinforcement sheet is provided on a surface side of the folded sanitary napkin with covering a portion of the folding line, the reinforcement sheet is bent at a position corresponding to the folding line without forming crease, and portions of the leakage preventing walls located corresponding to the portion across which the folding line extends, are urged onto an outer surface of a bent portion of the reinforcement sheet by the elastic tension force.

In the napkin package, the reinforcement sheet is provided on the surface of the sanitary napkin in the condition where the sanitary napkin is folded. In the portion of the sanitary napkin folded along the folding line, the reinforcement sheet is bent to form a bent or curved portion without forming crease, and the leakage preventing walls are urged onto an outer surface of the bent portion of the reinforcement sheet. Thus, in the folded condition of the sanitary napkin, folding pleat, permanent twisting or corrugation is hardly formed in the leakage preventing walls. When the napkin package is opened and the sanitary napkin is developed, the leakage preventing walls can be raised with superior restoring ability to sufficiently achieve side leakage blocking effect by the leakage preventing walls as worn on the wearer's body.

For instance, it is preferred that the reinforcement sheet is provided a bending resistance greater than or equal to 40 mm and smaller than or equal to 200 mm as measuring the bending resistance per 20 mm width in the longitudinal direction of the sanitary napkin by a 45° cantilever testing machine.

When the bending resistance falls within the range set forth above, the reinforcement sheet can form the curved portion without forming crease as placed inside of the folded sanitary napkin. On the other hand, this prevents the reinforcement sheet from unnecessarily pressing portions of the sanitary napkin other than the folding line in the leakage preventing walls.

In the further preferred construction, the sanitary napkin has extension portions on both sides of the leakage preventing walls, on back surface of the extension portion, adhesive layers being provided for securing the sanitary napkin on an underwear as worn, the extension portions being folded toward the surface along longitudinally extending folding lines located laterally outside of the leakage preventing walls, and the reinforcement sheet is releasably adhered on the adhesive layers.

Since the reinforcement sheet can serve as a protective sheet for covering the adhesive layers, it becomes unnecessary to provide a reinforcement sheet separately from the protective sheet.

On the other hand, the sanitary napkin may be folded along the folding line and at least one additional folding line, the additional folding line extends across a region where the leakage preventing walls are not formed, and the reinforcement sheet is placed not in opposition to a region where the additional folding line is provided.

As set forth above, by providing the reinforcement sheet for the portion where the folding line extends across the leakage preventing walls and by not providing the reinforcement sheet for the portion where the folding line does not extend across the leakage preventing walls, the reinforcement sheet is not required to be unnecessarily large.

According to the second aspect of the present invention, a napkin package comprises:

a sanitary napkin having a liquid absorbing surface and leakage preventing walls extending longitudinally along both sides of the liquid absorbing surface and elastically raised to project from the liquid absorbing surface, the sanitary napkin being folded along at least one folding line extending across respective leakage preventing walls;

a packaging sheet wrapping the sanitary napkin in folded condition for forming the napkin package; and means for forming a support surface located inside of folded portion of the sanitary napkin in opposition to at least one folding line and supporting fractions of the sanitary napkin on both sides of the folding line in spaced apart relationship.

According to the third aspect of the present invention, a napkin package comprises:

a sanitary napkin having a liquid absorbing surface and leakage preventing walls extending longitudinally along both sides of the liquid absorbing surface and elastically raised to project from the liquid absorbing surface, the sanitary napkin being folded along at least one folding line extending across respective leakage preventing walls;

a packaging sheet wrapping the sanitary napkin in folded condition for forming the napkin package; and means disposed between fractions of the sanitary napkin located on both sides of the folding line, for providing a rounded support surface located inside of folded portion of the sanitary napkin, on which the leakage preventing walls are urged by an elastic biasing force.

BRIEF DESCRIPTION OF THE DRAWINGS

The present invention will be understood more fully from the detailed description given hereinafter and from the accompanying drawings of the preferred embodiment of the present invention, which, however, should not be taken to be limitative to the invention, but are for explanation and understanding only.

In the drawings.

DESCRIPTION OF THE PREFERRED EMBODIMENT

The present invention will be discussed hereinafter in detail in terms of the preferred embodiments of a napkin package according to the present invention with reference to the accompanying drawings. In the following description, numerous specific details are set forth in order to provide a thorough understanding of the present invention. It will be obvious, however, to those skilled in the art that the present invention may be practiced without these specific details. In other instance, well-known structure is not shown in detail in order to avoid unnecessary obscurity of the present invention.

Figure 1:
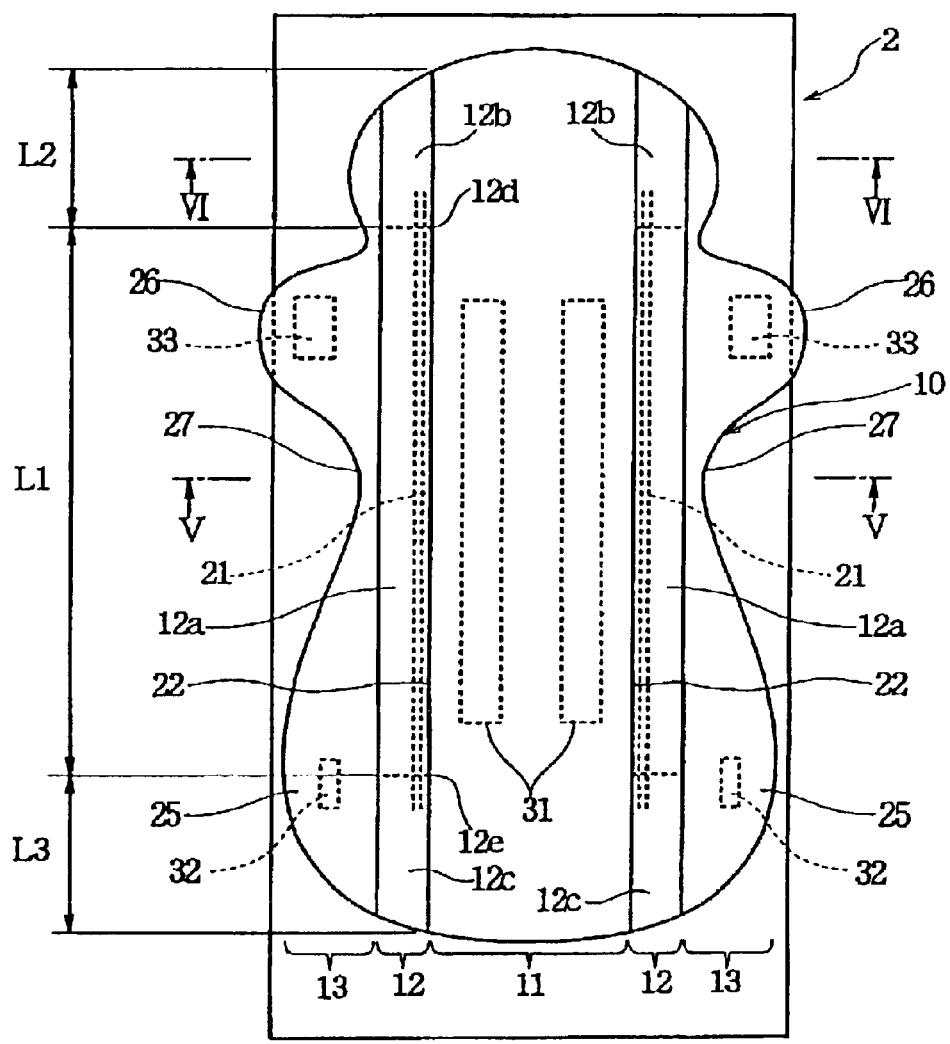
FIG. 1 is a plan view showing the first embodiment of a sanitary napkin and a packaging sheet according to the present invention in developed condition.
Figure 2:
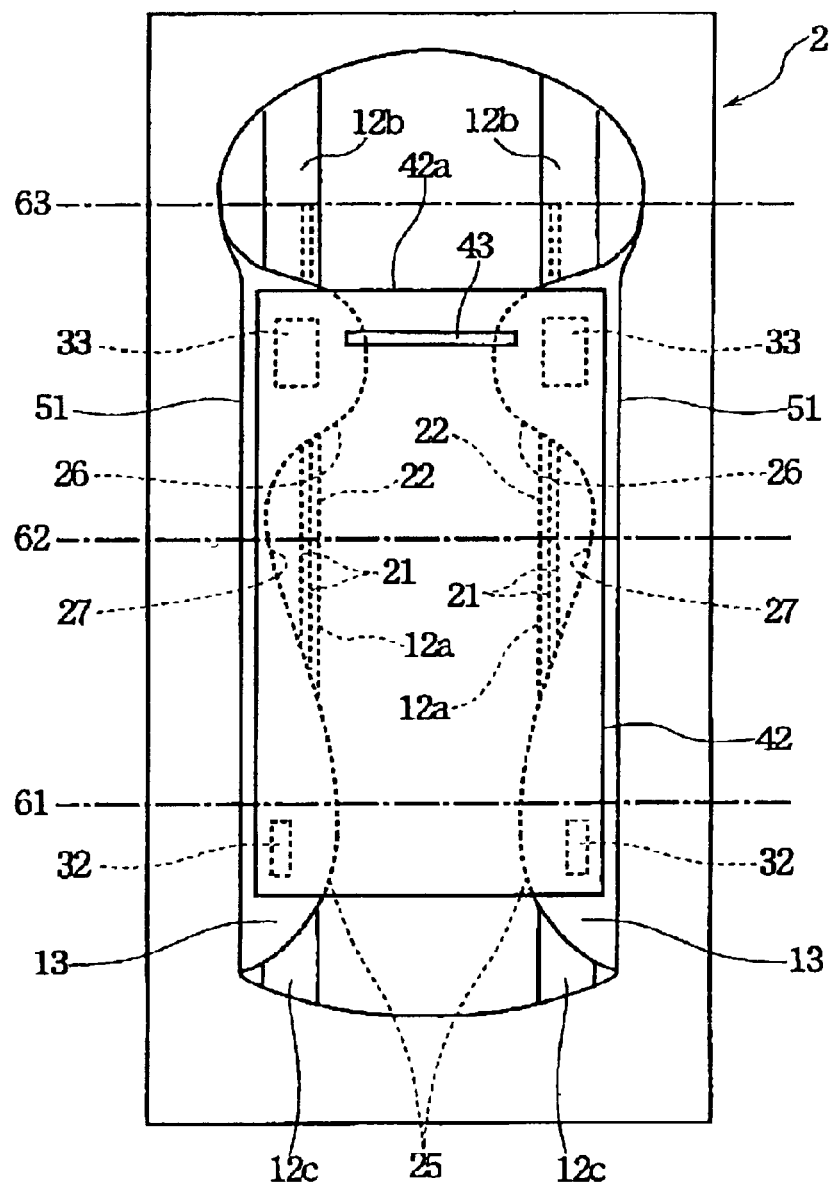
FIG. 2 is a plan view showing a condition where lateral side portions of the sanitary napkin are folded.
Figure 3A:
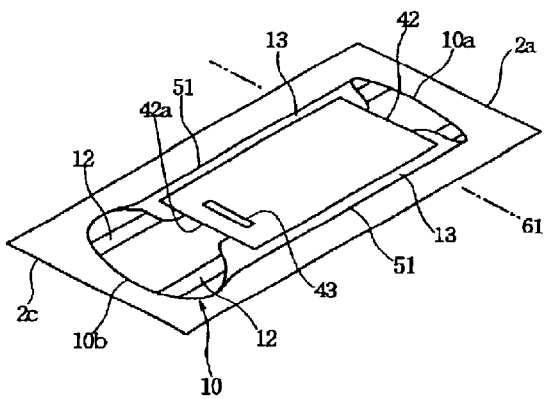
FIGS. 3A to 3E are perspective views showing a process of formation of a napkin package.
Figure 3B:
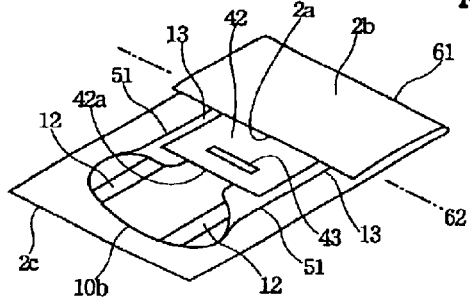
Figure 3C:
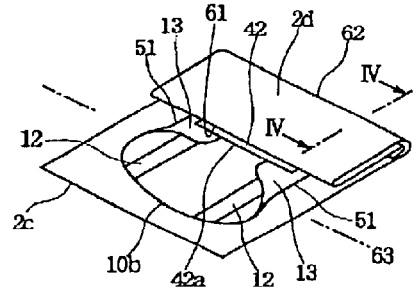
Figure 3D:
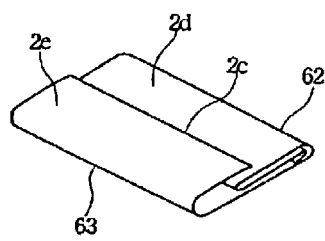
Figure 4:
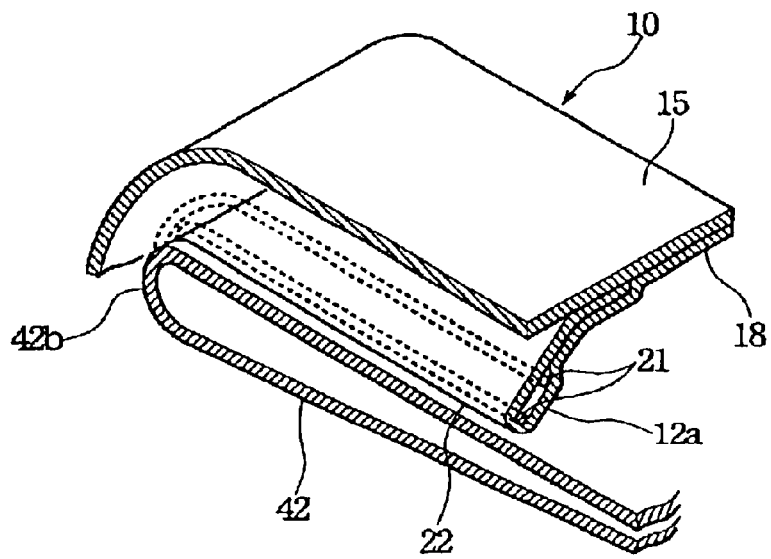
FIG. 4 is a sectional perspective view taken along the line IV—IV of FIG. 3C, for showing a relationship between a folding line of the sanitary napkin and a curved portion of a reinforcement sheet.
Figure 5:
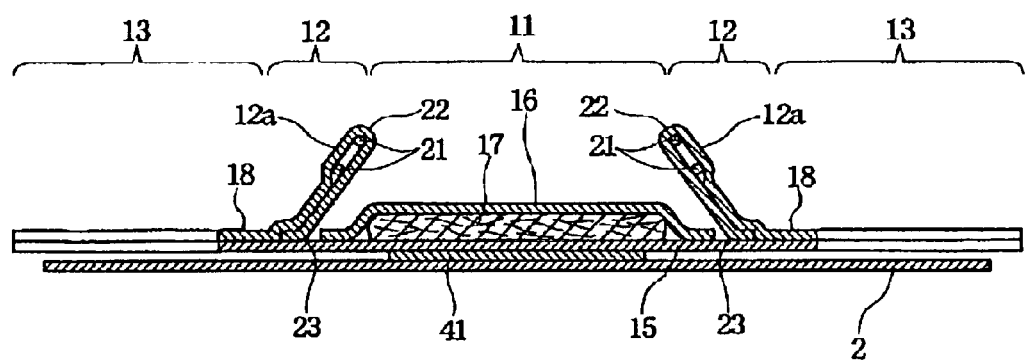
FIG. 5 is a section taken along the line V—V of FIG. 1.
Figure 6:
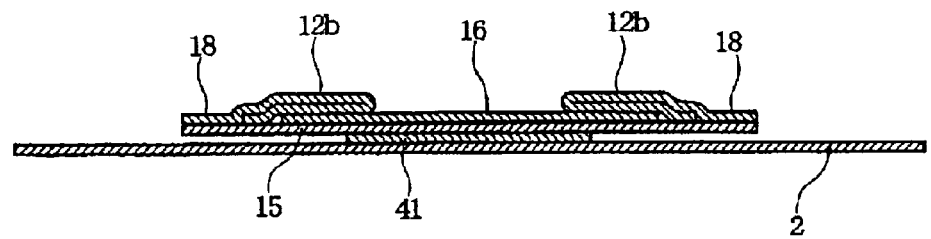
FIG. 6 is a section taken along the line VI—VI of FIG. 1.
Figure 7:
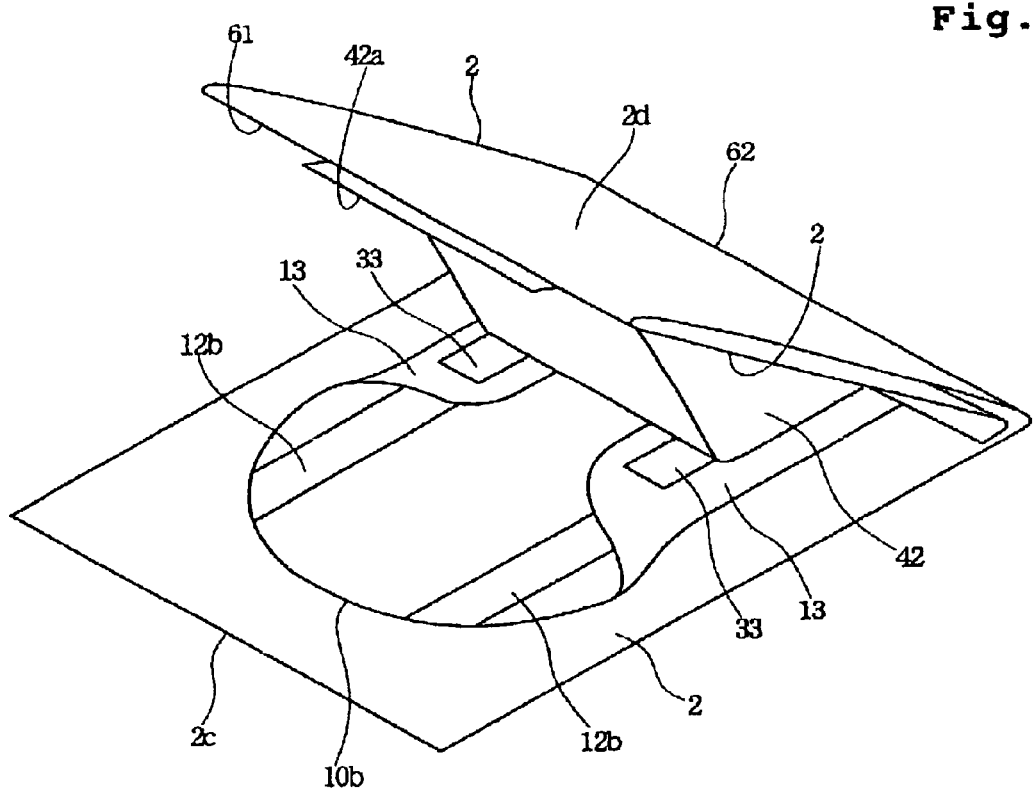
FIG. 7 is a perspective view showing a condition in a midway of opening of the napkin package.

FIG. 1 is a plan view of the first embodiment of a napkin package according to the present invention, shown in a condition where a packaging sheet and a sanitary napkin are developed; FIG. 2 is a plan view showing a condition where lateral side portions of the sanitary napkin are folded; FIGS. 3A to 3E are perspective views showing a process of formation of the napkin package; FIG. 4 is a sectional perspective view taken along the line IV—IV of FIG. 3C, for showing a relationship between a folding line of the sanitary napkin and a curved portion of a reinforcement sheet; FIG. 5 is a section taken along the line V—V of FIG. 1; FIG. 6 is a section taken along the line VI—VI of FIG. 1; and FIG. 7 is a perspective view showing a condition in a midway of opening of the napkin package.

Figure 3E:
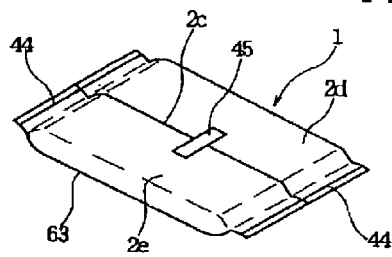

FIG. 3E shows the preferred embodiment of a napkin package according to the present invention. As shown in FIG. 1, a napkin package 1 is formed by folding a packaging sheet 2 and a sanitary napkin 10 together.

The packaging sheet 2 is formed of heat fusible material, such as a film formed from thermoplastic resin, e.g. polyethylene (PE) or the like; a spun bonded non-woven fabric formed of thermoplastic synthetic fiber; a three layer laminated sheet of spun bonded non-woven fabric/melt brown non-woven fabric/spun bonded non-woven fabric formed of thermoplastic resin, and so forth.

The sanitary napkin 10 is longitudinally elongated shape defining a liquid absorbing region 11 at a center portion thereof. On both lateral sides of the liquid absorbing region 11, longitudinally extending leakage preventing zones 12 are provided. On the other hand, on laterally outsides of the leakage preventing zones 12, extension portions 13 are provided.

As shown in FIGS. 5 and 6, a back sheet 15 of the sanitary napkin 10 is formed from a high polymer resin film of polyethylene (PE), polypropylene (PP), copolymer of ethylene and vinyl acetate (EVA) and so forth, and more preferably is a moisture permeable film formed with fine apertures by elongation with blending filler to the material of the film.

In the liquid absorbing region 11, an absorbent core 17 is provided on the back sheet 15. The absorbent core 17 is formed with a mixture prepared by mixing superabsorbent polymer into crushed pulp, a superabsorbent polymer wrapped with cellulose sheet, cellulose fibers fabricated into a sheet form and so forth.

In the liquid absorbing region 11, a surface of the absorbent core 17 is covered with a liquid permeable surface sheet 16. The surface sheet 16 is formed from a non-woven fabric fabricated from synthetic fibers provided hydrophilic treatment, a synthetic resin film formed with a large number of liquid permeable apertures and so forth. The back sheet 15 and the surface sheet 16 are bonded in a peripheral portion of the absorbent core 17 by means of an adhesive, heat seal and so forth.

In the leakage preventing zones 12 and the extension portions 13, leakage preventing sheets 18 are formed from a through air non-woven fabric which is formed from synthetic fibers of PE, PP, Polyethylene terephthalate (PET) or the like; a composite synthetic fibers of PE and PP; a composite synthetic fibers of PE and PET, and so forth. A fineness of the fibers forming the through air non-woven fabric is preferably in a range of 1.1 to 6.7 dtex, and a basis weight is preferably within a range of 10 to 40 g/m$^2$. As another example of the leakage preventing sheet 18, a through air non-woven fabric laminated a resin film, a spun bonded non-woven fabric formed from fibers of PE, PP or the like may be applicable. On the other hand, the leakage preventing sheet 18 is preferably provided water proofing treatment so as to block the liquid.

The leakage preventing sheet 18 is folded into two ply leakage preventing zones 12 on both lateral sides of the liquid absorbing region 11.

The leakage preventing zones 12 form leakage preventing walls 12a in a portion of a longitudinal length L1 in the plan view of FIG. 1. As shown in FIG. 5, in these leakage preventing walls 12a, free edge portions 22 are located away from the surface sheet 16. On the other hand, base end portions 23 of the leakage preventing walls 12a are bonded by adhesive or heat seal on the surface of the back sheet 15. On the other hand, in the leakage preventing walls 12a, a plurality of elastic members 21 extending in the longitudinal direction are sandwiched between folded two ply leakage preventing sheets 18. The elastic members 21 are formed from strip form or string form natural rubber or synthetic rubber, string form urethane type resin, strip form olefin type resin and so forth. The elastic members 21 are jointed or fixed on the leakage preventing sheet 18 in a condition preliminarily applied longitudinal tension stress to apply a longitudinal elastic tension force or shrinking force on the leakage preventing walls 12a.

Front side regions of the leakage preventing zones 12 in a length L2 are joining portions 12b. In these joining portions 12b, the folded two ply leakage preventing sheets 18 are fallen on the surface sheet 16 and the entire leakage preventing zones 12 are bonded by the adhesive or heat seal on the surface of the surface sheet 16, as shown in FIG. 6. On the other hand, rear side regions of the leakage preventing zones 12 in a length L3 are also joining portions 12c.

Similarly to the joining portions 12b of FIG. 6, the entire leakage preventing zones 12 are bonded on the surface of the surface sheet 16 by the adhesive or heat seal.

When the sanitary napkin 10 is in free condition, a longitudinal tension force is applied to the leakage preventing walls 12a by the elastic members 21 provided in the leakage preventing walls 12a to bow the liquid absorbing side surface of the sanitary napkin 10 in concave fashion. As a result, the free edge portions 22 of the leakage preventing walls 12a are placed away from the surface sheet 16 and thus the leakage preventing walls 12a are raised.

In order to ensure raising of the leakage preventing walls 12a when the sanitary napkin 10 is in free condition, the elastic tension force of the elastic members 21 in longitudinal direction has to be applied appropriately. The elastic tension force is preferably greater than or equal to 0.196N and less than or equal to 1.96N measured as a force in the contracting direction acting between a front end 12d and a rear end 12e of one leakage preventing wall 12a when the sanitary napkin 10 is placed in flat condition. When the foregoing force is smaller than 0.196N, it becomes not possible to ensure raising of the leakage preventing walls 12a three-dimensionally. When the foregoing force becomes greater than 1.96N, degree of bowing of the sanitary napkin in free condition becomes too large to make fitting force of the free edge portions 22 of the leakage preventing walls 12a as worn too large.

In the extension portions 13 of the sanitary napkin 10, the leakage preventing sheet 18 extends laterally outward to be overlapped with the back sheet 15 to be bonded to the latter using the adhesive or by heat seal. Thus, the back sheet 15 and the leakage preventing sheet 18 are integrated with each other.

The extension portions 13 are further extended laterally outward on outer sides of the leakage preventing zones 12 in the rear portion of the sanitary napkin 10 to form flap portions 25. In the shown embodiment, the sanitary napkin 10 is adapted to be worn while sleeping so that both flap portions 25 and the liquid absorbing region 11 located between the flap portions 25 may cover hip portion of the wearer. On the other hand, the extension portions 13 are further extended laterally on both sides in the front portion of the sanitary napkin 10 to form wing portions 26.

On the outer surface of the back sheet 15, pressure sensitive adhesive layers 31 extending in longitudinal direction in two lines are formed. On the other hand, on the back sides of the flap portions 25, pressure sensitive adhesive layers 32 are formed. Also, on the back sides of the wing portions 26, pressure sensitive adhesive layers 33 are formed. The pressure sensitive adhesive layers 31, 32 and 33 may be formed from hot-melt type adhesive or the like.

Next, process in formation of the napkin package 1 by folding the packaging sheet 2 and the sanitary napkin 10 together will be discussed.

As shown in FIGS. 5 and 6, a release sheet or paper 41 is fitted over the inner surface (upper surface) of the packaging sheet 2. The release sheet 41 is formed by forming a releasing layer, such as silicon resin or the like on the surface of a paper or the like. The release sheet 41 is of a size to cover the pressure sensitive adhesive layers 31 provided at the center portion on the back surface of the sanitary napkin 10. As shown in FIG. 1, the sanitary napkin 10 is set on the packaging sheet 2 and the pressure sensitive adhesive layers 31 are releasably adhered on the surface of the release sheet 41.

As shown in FIG. 2, the extension portions 13 on both lateral sides of the sanitary napkin 10 are folded toward the surface side of the sanitary napkin 10 along longitudinally extending folding lines 51 located outside of the leakage preventing zones 12. The flap portions 25 and the wing portions 26 as portions of the extension portions 13 are overlapped on the surface side of the sanitary napkin 10. Then, the pressure sensitive adhesive layers 32 and the pressure sensitive adhesive layers 33 located on the back side of the sanitary napkin 10 are directed toward proximal side from the sheet surface of FIG. 2. On the other hand, in the condition shown in FIG. 2, within recessed portions 27 between the flap portions 25 and the wing portions 26, the leakage preventing walls 12a and the free edge portions 22 appear or expose.

As shown in FIG. 2, a reinforcement sheet 42 is provided on the folded flap portions 25 and the wing portions 26. By the reinforcement sheet 42, portions of the leakage preventing walls 12a appearing in the recessed portions 27 are covered.

The reinforcement sheet 42 employed in the shown embodiment is a release sheet, and is formed by forming a release layer of silicon resin or the like on the surface of slightly thick resin film. Then, the reinforcement sheet 42 is releasably adhered to the pressure sensitive adhesive layers 32 formed on the flap portions 25 and the pressure sensitive adhesive layers 33 formed on the wing portion 26.

The packaging sheet 2 and the sanitary napkin 10 shown in FIG. 2 are folded together along a first folding line 61, a second folding line 62 and a third folding line 63 extending in lateral direction. Here, the second folding line 62 is set across the leakage preventing walls 12a appearing in the recessed portions 27. On the other hand, the third folding line 63 is also set across the leakage preventing zones 12. Here, the third folding line 63 extends across the joining portions 12b located out of the region where the leakage preventing walls 12a are provided.

By the first folding line 61 shown in FIG. 3A, a rear end 2a of the packaging sheet 2 and a rear end 10a of the sanitary napkin 10 are folded to overlap on the reinforcement sheet 42. FIG. 3B shows a condition where the packaging sheet 2 and the sanitary napkin 10 are folded along the first folding line 61.

Next, along the second folding line 62, the packaging sheet 2 and the sanitary napkin 10 are folded to place the first folding line 61 on the surface of the reinforcement sheet 42. The condition folded along the second folding line 62 is illustrated in FIG. 3C. On the outer surface of the reinforcement sheet 42, an adhesive layer 43 is provided slightly inside than a front end 42a thereof. In the condition shown in FIG. 3C, a region 2b located between the rear end 2a of the back surface of the packaging sheet 2 and the first folding line 61 is bonded on the outer surface of the reinforcement sheet 42 via the adhesive layer 43.

Furthermore, the packaging sheet 2 and the sanitary napkin 10 are further folded along the third folding line 63. Then, a front end 2c of the packaging sheet 2 and a front end 10b of the sanitary napkin 10 are overlapped on a region 2d located between the first folding line 61 and the second folding line 62 on the back surface of the packaging sheet 2. As a result, the packaging sheet 2 and the sanitary napkin 10 are placed in a condition folded for three times, as shown in FIG. 3D.

Subsequently, as shown in FIG. 3E, joint lines 44 are formed on both side portions of the packaging sheet 2 by heat seal. Furthermore, on the back surface of the packaging sheet 2, from a region 2e located between the front end 2c and the third folding line 63, to the region 2d, a seal strip 45 is bonded via the pressure sensitive adhesive layer to complete sealing of the napkin package 1.

Here, in the portion, across which the second folding line 62 extends, the leakage preventing walls 12a appear within the recessed portions 27 of the extension portions 13 of the sanitary napkin 10. To the free edge portions 22 of the leakage preventing walls 12a, the reinforcement sheet 42 is directly opposed. FIG. 4 shows a relationship between the leakage preventing walls 12a appearing in the recessed portions 27 and the reinforcement sheet 42 in the napkin package 1. The reinforcement sheet 42 has appropriate stiffness. Within the napkin package 1, the reinforcement sheet 42 is placed in opposition to inside of the second folding line 62. The reinforcement sheet 42 is curved without forming crease and a curved portion 42b is located inside of the second folding line 62.

The leakage preventing walls 12a exposed within the recessed portions 27 have the elastic members 21 extending in longitudinal direction. Therefore, the elastic force acts on the leakage preventing wall 12a in a direct away from the surface sheet 16 of the sanitary napkin 10 by the elastic tension force in the longitudinal direction. By this force, the free edge portions 22 of the leakage preventing walls 12a are pressed onto the outer surface of the reinforcement sheet 42. Also, even on the outer surface of the curved portion 42b, the free edge portions 22 are pressed along the outer surface of the reinforcement sheet 42. The reinforcement sheet 42 has stiffness not forming the crease by pressing force of the free edge portions 22. Within the napkin package 1, the reinforcement sheet 42 is placed in a condition maintaining the curved portion 42b.

Here, "not forming the crease" is not intended to mean forming permanent folding line in the reinforcement sheet 42 and intended to mean formation of the curved portion 42b maintaining a space within the folded portion of the reinforcement sheet 42.

Accordingly, the leakage preventing walls 12a exposed to the recessed portions 27 can maintain curved shape along the curved portions 42b. In the portion around the second folding line 62, extreme pleat is not formed so that formation of permanent pleat, twisting or corrugation can be restricted or eliminated in the leakage preventing walls 12a.

When the napkin package 1 is opened, the seal strip 45 shown in FIG. 3E is peeled off the region 2d. Then, the front end 2c of the packaging sheet 2 is pulled away from the region 2d. At this time, the packaging sheet 2 is separated along the joint lines 44. Next, as shown in FIG. 7, the portion of the first folding line 61 is pulled up. At this time, since the back surface of the packaging sheet 2 in the region 2b is bonded to the reinforcement sheet 42 via the adhesive layer 43, the reinforcement sheet 42 is lifted up together with the packaging sheet 2. Thus, the reinforcement sheet 42 is peeled off the pressure sensitive adhesive layers 33 formed on the sanitary napkin 10.

Thereafter, the packaging sheet 2 and the sanitary napkin 10 are unfolded and the reinforcement sheet 42 is peeled off the pressure sensitive adhesive layers 32. Then, the extension portions 13 are opened laterally. Thereafter, the release sheet 41 is peeled off the pressure sensitive adhesive layers 31 to take out the sanitary napkin 10 in developed condition.

In the sanitary napkin 10 after opening the package, since elastic restoring force can be maintained by abutting the free edge portions 22 of the leakage preventing walls 12a located at the portion where the second folding line 62 extends thereacross, onto the curved portion 42b of the reinforcement sheet 42, the leakage preventing walls 12a can certainly be raised from the surface side of the sanitary napkin 10 after developing the sanitary napkin.

Upon use of such sanitary napkin 10, the sanitary napkin is fixedly fitted on a crotch part of an underwear by the pressure sensitive adhesive layers 31. Also, the flap portions 25 are secured on the inner surface of the underwear by the pressure sensitive adhesive layers 32. The wing portions 26 are turned outwardly from the side edges of the crotch part of the underwear to be secured on the outer surface of the crotch part by the pressure sensitive adhesive layers 33.

In the worn condition, the free edge portions 22 of the leakage preventing walls 12a having the elastic members 21 contact with wearer's skin to satisfactorily prevent side leakage of extra body fluid which cannot be absorbed by the absorbent core 17.

It should be noted that, in the first embodiment, the extension portions 13 are not overlapped on the leakage preventing zones 12 in the portion where the third folding line 63 extend thereacross, and thus the leakage preventing zones 12 are exposed, as shown in FIG. 2. However, the portion where the third folding line 63 extends thereacross, provides the joining portions 12b presenting outside of the leakage preventing walls 12a. Therefore, when the sanitary napkin 10 is folded, the leakage preventing walls 12a will never be affected by the third folding line 63.

Figure 8:
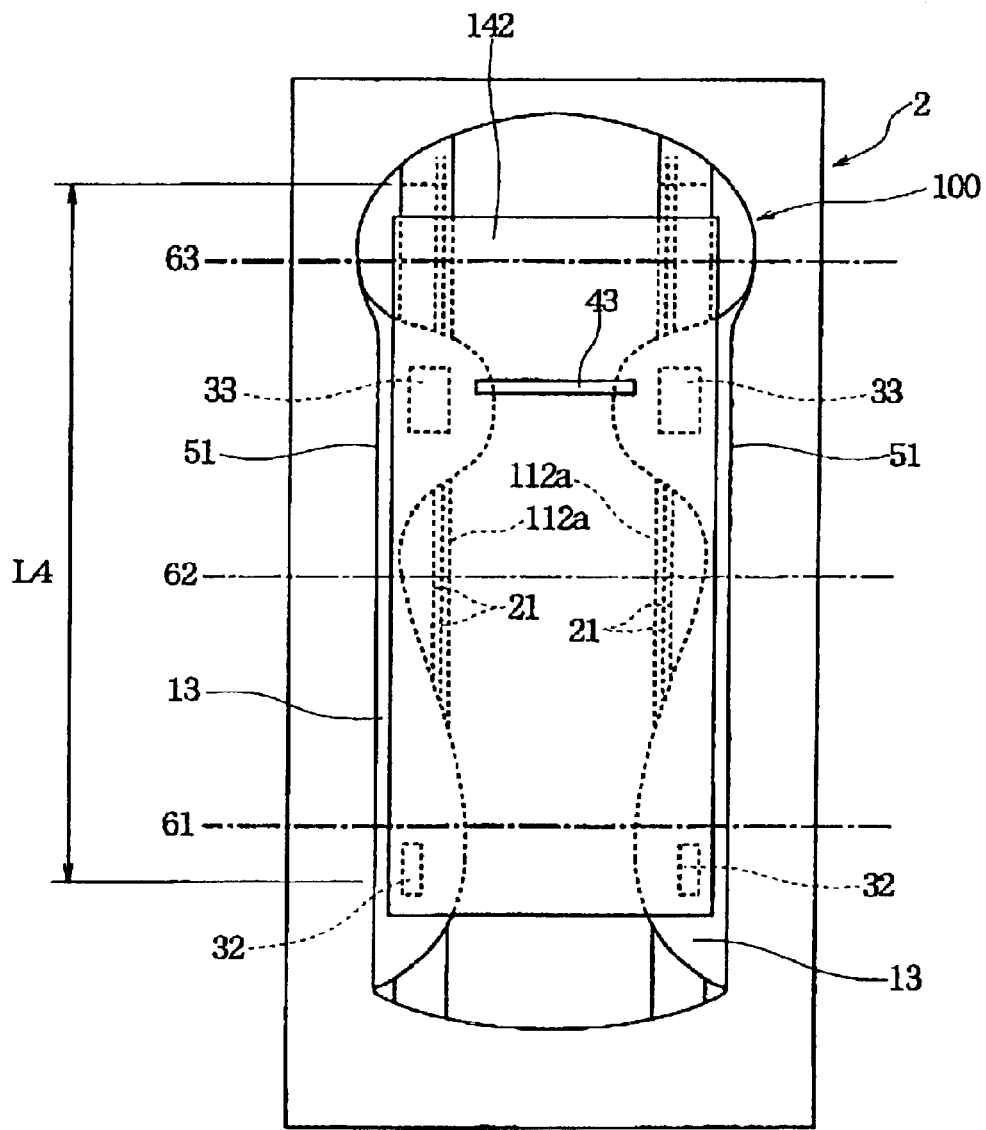
FIG. 8 is a plan view showing a modification of the present invention.

FIG. 8 is a modification of the first embodiment of the present invention. In the modification shown in FIG. 8, a sanitary napkin 100 is wrapped by the packaging sheet 2. The sanitary napkin 100 is the same as the sanitary napkin 10 shown in FIGS. 1 and 2 in the basic construction. In the sanitary napkin 100 shown in FIG. 8, leakage preventing walls 112a are provided with the elastic members 21 and thus can be raised. A longitudinal length L4 of the leakage preventing walls 112a is longer than the longitudinal length L1 of the leakage preventing walls 12a of the sanitary napkin 10 of FIG. 1.

The packaging sheet 2 and the sanitary napkin 100 shown in FIG. 8 are folded along the first folding line 61, the second holding line 62 and the third folding line 63 similarly to those shown in FIG. 2. However, different from the former embodiment, in the sanitary napkin 100, since the leakage preventing walls 112a are formed longer than the former embodiment, both of the second folding line 62 and the third folding line 63 extend across the leakage preventing walls 112a.

In addition, in the shown modification, a longitudinal length of a reinforcement sheet 142 is longer than the longitudinal length of the reinforcement sheet 42 shown in FIG. 2. Thus, at both portions where the second folding line 62 and the third folding line 63 respectively extend thereacross, the leakage preventing walls 112a are covered by the reinforcement sheet 142. In the condition formed into the napkin package by folding the packaging sheet 2 and the sanitary napkin 100 along the first folding line 61, the second folding line 62 and the third folding line 63, curved portions are formed in the reinforcement sheet 142 respectively at portion located inside of the portion where the second folding line 62 extends and at portion located inside of the portion where the third folding line 63 extends. The portions of the leakage preventing walls 112a located at the portions where the second folding line 62 and the third folding line 63 extend thereacross are elastically pressed onto the outer surface of the curved portion, respectively.

Accordingly, the leakage preventing walls 112a of the sanitary napkin 100 can be prevented from formation of folding pleat at both portions across which the second folding line 62 and the third folding line 63 extent. Thus, formation of permanent twisting or corrugation can be successfully prevented.

Next, the second embodiment of a napkin package according to the present invention will be discussed with reference to FIG. 9.

Figure 9:
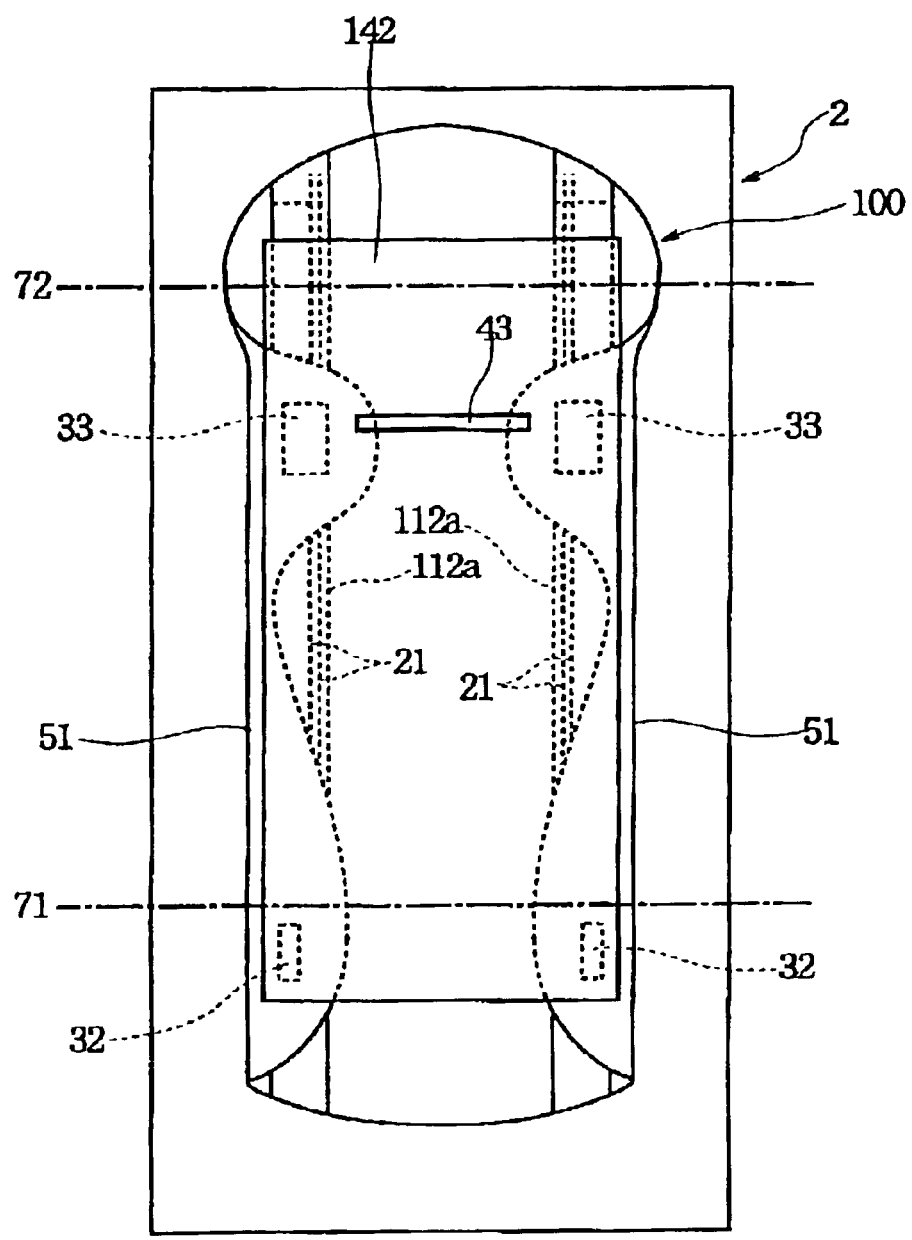
FIG. 9 is a plan view showing the second embodiment of a napkin package according to the present invention.

In the shown embodiment of FIG. 9, a structure of the packaging sheet 2 and the sanitary napkin 100 is identical to those shown in FIG. 8. In the embodiment shown in FIG. 9, the packaging sheet 2 and the sanitary napkin 100 are folded along two folding lines of a first folding line 71 and a second folding line 72 to form the napkin package.

The first folding line 71 is set substantially the same position as the first folding line 61 shown in FIG. 8, and the second folding line 72 is set substantially the same position as the third folding line 63 shown in FIG. 8.

In the portion across which the second folding line 72 extends, the leakage preventing walls 112a are located. However, in the portion where the second folding line 72 is set, the leakage preventing walls 112a are covered with the reinforcement sheet 142. Similarly to the embodiment shown in FIG. 8, the curved portion of the reinforcement sheet 142 is placed in opposition to inside of the sanitary napkin 100 folded along the second folding line 72. Therefore, in the portion where the second folding line 72 is provided, the folding pleat, permanent twisting or corrugation are hardly formed in the leakage preventing walls 112a.

It should be noted that, while the present invention has been disclosed in terms of the sanitary napkins 10 and 100 formed with large flap portions 25 extending laterally in the rear portion in respective of the embodiments, the present invention is effectively applicable for sanitary napkin which does not have large flap portions 25.

In case of the sanitary napkin having small or no flap portion extending laterally, the leakage preventing walls 12a or 112a are exposed in the portion across which the first folding line 61 or 71 extends, in the condition where lateral side portions of the sanitary napkin are folded as shown in FIGS. 2, 8 and 9. Even in such case, formation of folding pleat in the leakage preventing walls 12a or 112a can be prevented by covering the leakage preventing walls 12a or 112a by the reinforcement sheet 42 or 142.

It should be noted that when the elastic tension force to be applied to the leakage preventing walls 12a or 112a is in a range of 0.196N to 1.96N, a bending resistance of the reinforcement sheet 42 or 142 is preferably greater than or equal to 40 mm and smaller than or equal to 200 mm.

The bending resistance is measured by use of a 45° cantilever testing machine as defined in JIS L-1018 for the reinforcement sheet of the size of 300 mm in longitudinal length and 20 mm in width.

If the bending resistance is smaller than 40 mm, the elastic tension force of the elastic members 21 in the condition shown in FIG. 4, overcomes the stiffness of the reinforcement sheets 42, 142 to easily form crease in the reinforcement sheet. By such crease, when the leakage preventing walls 12a, 112a are depressed, the folding pleat can be formed in the leakage preventing walls 12a or 112a. On the other hand, if the bending resistance is in excess of 200 mm, restoring force to restore flat condition when the reinforcement sheet is bent, becomes excessively large to cause difficulty in formation of the curved portion inside of the folding line. Furthermore, difficulty can be encountered in folding the sanitary napkin and the packaging sheet to make it difficult to form the napkin package.

It should be noted that the reinforcement sheet 42 or 142 in the shown embodiment also serves as release sheet for the pressure sensitive adhesive layers 32 and 33. However, it is also possible to use the reinforcement sheet not serving as release sheet in opposition to the leakage preventing walls. As the reinforcement sheet, a foamed sheet of polyethylene or a porous resin film formed with apertures in random direction.

EXAMPLE

The napkin package similar to that illustrated in FIG. 3E was produced using the sanitary napkin and the packaging sheet illustrated in FIGS. 1 to 7.

The elastic tension force to be applied to the leakage preventing walls in the longitudinal direction was set 0.49N.

Example 1

As the reinforcement sheet, a release paper having a basis weight of 40 g/m$^2$ was used. The bending resistance per 20 mm width as measured by the 45° cantilever testing machine was 78.0 mm.

Example 2

As the reinforcement sheet, a non-crepe paper having a basis weight of 30 g/m$^2$ was used. The bending resistance per 20 mm width as measured by the 45° cantilever testing machine was 74.6 mm.

Comparative Example 1

As the reinforcement sheet, a non-woven fabric having a basis weight of 17 g/m$^2$ was used. The non-woven fabric was a laminated sheet of spun bonded non-woven fabric/melt brown non-woven fabric/spun bonded non-woven fabric formed from PP fibers. The bending resistance per 20 mm width as measured by the 45° cantilever testing machine was 38.2 mm.

Comparative Example 2

As the reinforcement sheet, a paper material having a basis weight of 185.8 g/m$^2$ was used. The paper material was prepared by two ply of non-crepe paper having a basis weight of 67.9 g/m$^2$, and two pieces of the non-crepe papers were bonded by an adhesive having a basis weight of 50 g/m$^2$. The bending resistance per 20 mm width as measured by the 45° cantilever testing machine was 201.8 mm.

After forming the napkin package shown in FIG. 3E, the package was left for twenty-four hours. Thereafter, the sanitary napkin was taken out by opening the package and observed visually. In the examples 1 and 2, no folding pleat was formed in the leakage preventing walls and folding of the sanitary napkin could be done easily. In contrast to this, folding pleat was observed in the comparative example 1. On the other hand, in case of the comparative example 2, folding of the sanitary napkin was difficult.

Therefore, preferred bending resistance of the reinforcement sheet is in a range greater than or equal to 40 mm and smaller than or equal to 200 mm, and more preferably in a range greater than or equal to 50 mm and smaller than or equal to 100 mm.

As set forth above, with the present invention, in the napkin package formed by wrapping the sanitary napkin having the leakage preventing walls three-dimensionally raised by elastic tension force, with the packaging sheet, permanent folding pleat, permanent twisting or corrugation will never be formed in the leakage preventing wall.

Although the present invention has been illustrated and described with respect to exemplary embodiment thereof, it should be understood by those skilled in the art that the foregoing and various other changes, omission and additions may be made therein and thereto, without departing from the spirit and scope of the present invention. Therefore, the present invention should not be understood as limited to the specific embodiment set out above but to include all possible embodiments which can be embodied within a scope encompassed and equivalent thereof with respect to the feature set out in the appended claims.

What is claimed is:

1. A napkin package formed by wrapping a sanitary napkin in folded condition with a packaging sheet, wherein
   said sanitary napkin having longitudinally extending leakage preventing walls on both sides of a liquid absorbing portion, said leakage preventing walls being provided with elastic members for applying an elastic tension force in a longitudinal direction to place free edge portions of said leakage preventing walls away from a surface of said liquid absorbing portion;
   said sanitary napkin being folded along a folding line extending across said leakage preventing walls with mating said surface;
   a reinforcement sheet being provided on a surface side of the folded sanitary napkin with covering a portion of said folding line, said reinforcement sheet being bent at a position corresponding to said folding line without forming crease, and portions of said leakage preventing walls located corresponding to the portion across which said folding line extends, being urged onto an outer surface of a bent portion of said reinforcement sheet by the elastic tension force.

2. A napkin package as set forth in claim 1, wherein said reinforcement sheet is provided a bending resistance greater than or equal to 40 mm and smaller than or equal to 200 mm as measuring the bending resistance per 20 mm width in the longitudinal direction of said sanitary napkin by a 45° cantilever testing machine.

3. A napkin package as set forth in claim 1, wherein said sanitary napkin has extension portions on both sides of said leakage preventing walls, on a back surface of said extension portion, adhesive layers being provided for securing said sanitary napkin on an underwear as worn, said extension portions being folded toward said surface side along longitudinally extending folding lines located laterally outside of said leakage preventing walls, and said reinforcement sheet is releasably adhered on said adhesive layers.

4. A napkin package as set forth in claim 1, wherein said sanitary napkin is folded along said folding line and at least one additional folding line, said additional folding line extends across a region where said leakage preventing walls are not formed, and said reinforcement sheet is placed not in opposition to a region where said additional folding line is provided.

5. A napkin package comprising:
   a sanitary napkin having a liquid absorbing surface and leakage preventing walls extending longitudinally along both sides of said liquid absorbing surface and elastically raised to project from said liquid absorbing surface, said sanitary napkin being folded along at least one folding line extending across respective leakage preventing walls;
   a packaging sheet wrapping said sanitary napkin in folded condition for forming said napkin package; and
   means for forming a support surface located inside of folded portion of said sanitary napkin in opposition to said at least one folding line and supporting fractions of said sanitary napkin on both sides of said folding line in spaced apart relationship.

6. A napkin package comprising:

a sanitary napkin having a liquid absorbing surface and leakage preventing walls extending longitudinally along both sides of said liquid absorbing surface and elastically raised to project from said liquid absorbing surface, said sanitary napkin being folded along at least one folding line extending across respective leakage preventing walls;

a packaging sheet wrapping said sanitary napkin in folded condition for forming said napkin package; and means disposed between fractions of said sanitary napkin located on both sides of said folding line, for providing a rounded support surface located inside of folded portion of said sanitary napkin, on which said leakage preventing walls are urged by an elastic biasing force.

* * * * *